US011558534B2

(12) United States Patent
Numasawa et al.

(10) Patent No.: US 11,558,534 B2
(45) Date of Patent: Jan. 17, 2023

(54) IMAGING MODULE, ENDOSCOPE, AND CATHETER

(71) Applicant: Fujikura Ltd., Tokyo (JP)

(72) Inventors: Yoshinobu Numasawa, Sakura (JP); Kenichi Ishibashi, Sakura (JP); Daisuke Murakami, Sakura (JP); Takeshi Ishizuka, Sakura (JP)

(73) Assignee: FUJIKURA LTD., Tokyo (JP)

( * ) Notice: Subject to any disclaimer, the term of this patent is extended or adjusted under 35 U.S.C. 154(b) by 0 days.

(21) Appl. No.: 16/967,023

(22) PCT Filed: Nov. 7, 2018

(86) PCT No.: PCT/JP2018/041368
§ 371 (c)(1),
(2) Date: Aug. 3, 2020

(87) PCT Pub. No.: WO2019/155704
PCT Pub. Date: Aug. 15, 2019

(65) Prior Publication Data
US 2021/0037169 A1 Feb. 4, 2021

(30) Foreign Application Priority Data
Feb. 8, 2018 (JP) .............................. JP2018-021215

(51) Int. Cl.
H04N 5/225 (2006.01)
A61B 1/05 (2006.01)
A61B 1/06 (2006.01)

(52) U.S. Cl.
CPC ........... H04N 5/2253 (2013.01); A61B 1/051 (2013.01); A61B 1/0676 (2013.01);
(Continued)

(58) Field of Classification Search
CPC ... H04N 5/2253; H04N 5/2252; H04N 5/2256
See application file for complete search history.

(56) References Cited

U.S. PATENT DOCUMENTS 10,016,118 B2 * 7/2018 Konomura ......... A61B 1/00057
2004/0027459 A1 2/2004 Segawa et al.
(Continued)

FOREIGN PATENT DOCUMENTS

JP H08117184 A 5/1996
JP H11253398 A 9/1999
(Continued)

OTHER PUBLICATIONS

English Translation of International Search Report issued in corresponding International Application No. PCT/JP2018/041368, dated Jan. 22, 2019 (2 pages).

Primary Examiner — Jonathan R Messmore
(74) Attorney, Agent, or Firm — Osha Bergman Watanabe & Burton LLP

(57) ABSTRACT

An imaging module includes: a support substrate that includes a first surface, a second surface on an opposite side of the first surface, and a first mounting terminal disposed on the first surface; a planar light emitter including a light-emitting face, and a light-emitter terminal disposed on the first surface of the support substrate and connected to the first mounting terminal; and a solid-state image sensing device disposed adjacent to the planar light emitter and that includes a light-incident surface that has a quadrangular shape in plan view and that captures an image of an imaging object that is irradiated with light emitted from the light-emitting face.

11 Claims, 9 Drawing Sheets

(52) U.S. Cl.
 CPC ......... *H04N 5/2252* (2013.01); *H04N 5/2256* (2013.01); *H04N 2005/2255* (2013.01)

(56) References Cited

U.S. PATENT DOCUMENTS

| | | | |
|---|---|---|---|
| 2004/0225189 A1 | 11/2004 | Kimoto et al. | |
| 2008/0091064 A1* | 4/2008 | Laser ..................... | A61B 1/267 600/109 |
| 2009/0062605 A1 | 3/2009 | Orihara et al. | |
| 2011/0025843 A1* | 2/2011 | Oggier ............... | G02B 19/0019 348/135 |
| 2015/0038787 A1* | 2/2015 | Nishimura ........... | A61B 1/0638 600/109 |
| 2015/0319409 A1* | 11/2015 | Imamura ................ | H04N 5/247 348/135 |
| 2018/0245490 A1* | 8/2018 | Hori ..................... | H04N 5/2253 |
| 2019/0142264 A1* | 5/2019 | Bos ..................... | A61B 1/0684 600/188 |

FOREIGN PATENT DOCUMENTS

| | | | |
|---|---|---|---|
| JP | 2005124963 A | 5/2005 | |
| JP | 2008118568 A | 5/2008 | |
| JP | 2009-056058 A | 3/2009 | |
| JP | 2017195960 A | 11/2017 | |
| WO | 2004/096029 A1 | 11/2004 | |

\* cited by examiner

IMAGING MODULE, ENDOSCOPE, AND CATHETER

TECHNICAL FIELD

The present invention relates to an imaging module, an endoscope, and a catheter.

This application claims priority from Japanese Patent Application No. 2018-021215 filed on Feb. 8, 2018, the contents of which are incorporated herein by reference in their entirety.

BACKGROUND

Conventionally, an endoscope including a light guide fiber for illumination is known (for example, refer to Patent Document 1). The endoscope includes a sheath surrounding a lens provided as the distal end thereof, and a light guide fiber provided between the sheath and the lens. Light guided by the light guide fiber is emitted from the distal end of the endoscope.

PATENT LITERATURE (Patent Literature 1) Japanese Unexamined Patent Application, First Publication No. 2017-195960

However, there are the following issues in the endoscope including the light guide fiber. The light guide fiber has rigidity and therefore cannot be sufficiently bent. Consequently, flexibility in an endoscope including the light guide fiber is degraded. In the case where an optical fiber is broken due to bending of the light guide fiber, light from a light source cannot be guided to the distal end of the light guide fiber. It is necessary to increase the numbers of optical fibers constituting the light guide fiber in order to obtain sufficient illuminance, in the case, the cross-sectional area of the light guide fibers increases, and therefore it is not possible to provide an endoscope having a small-diameter. Since the light guide fiber is arranged in the entire length of the endoscope, a working channel having a sufficient size in a plane of projection of the endo scope cannot be ensured. Additionally, the material costs and the assembling costs of the light guide fiber increase, and therefore it is not possible to provide an inexpensive endoscope.

SUMMARY

One or more embodiments of the present invention provide an imaging module that has a small diameter and can achieve an endoscope obtaining sufficient illuminance without using a light guide fiber, an endoscope including the imaging module, and a catheter including the endoscope.

An imaging module according to one or more embodiments of the present invention includes: a support substrate that includes a first surface, a second surface located on an opposite side of the first surface, and a first mounting terminal provided on the first surface; a planar light emitter that includes a light-emitting face and a light-emitter terminal connected to the first mounting terminal, and is mounted on the first surface of the support substrate; and a solid-state image sensing device that includes a light-incident surface formed in a quadrangular shape in plan view, is disposed adjacent to the planar light emitter, and captures an image of an imaging object to be irradiated with light emitted from the light-emitting face.

In the imaging module according to one or more embodiments of the present invention, the support substrate may include a second mounting terminal that is disposed adjacent to the first mounting terminal and is provided on the first surface, and the solid-state image sensing device may be connected to the second mounting terminal and may be mounted on the first surface of the support substrate.

The imaging module according to one or more embodiments of the present invention may further include: a first external terminal that is provided on the second surface of the support substrate and is electrically connected to the planar light emitter via the first mounting terminal; and a second external terminal that is provided on the second surface of the support substrate and is electrically connected to the solid-state image sensing device via the second mounting terminal.

The imaging module according to one or more embodiments of the present invention may further include an imaging unit (i.e., imager) that is a body separate from the support substrate, wherein the solid-state image sensing device may be electrically connected to the imaging unit, the support substrate may include a through hole that is located adjacent to the first mounting terminal and penetrates through the support substrate, the imaging unit may be fixed to and inserted into the through hole, and the solid-state image sensing device of the imaging unit may be disposed adjacent to the planar light emitter.

The imaging module according to one or more embodiments of the present invention may further include a first external terminal that is provided on the second surface of the support substrate and is electrically connected to the planar light emitter via the first mounting terminal.

The imaging module according to one or more embodiments of the present invention may further include a cover member that is provided on the first surface of the support substrate, is formed of a transparent material, and covers the planar light emitter and the solid-state image sensing device.

In the imaging module according to one or more embodiments of the present invention, when seen in a cross-sectional view in a direction perpendicular to the light-incident surface, a distance from the first surface to the light-incident surface may be greater than a distance from the first surface to the light-emitting face, and the cover member may include: an exposed area at which the light-incident surface is exposed; and an outer surface that reaches an edge of the support substrate from an outer-periphery of the light-incident surface in the cross-sectional view.

In the imaging module according to one or more embodiments of the present invention, the outer surface of the cover member may have a curved surface in the cross-sectional view.

In the imaging module according to one or more embodiments of the present invention, the cover member may include a coating portion that coats the light-incident surface.

In the imaging module according to one or more embodiments of the present invention, a plurality of the planar light emitters may be provided, and the plurality of the planar light emitters may be arranged so as to surround the solid-state image sensing device in plan view.

In the imaging module according to one or more embodiments of the present invention, the support substrate may include: a controller that controls light emission of the planar light emitter; a control wiring that connects the controller to the first mounting terminal; and a control terminal that is provided on the second surface and is electrically connected to the controller.

An endoscope according to one or more embodiments of the present invention includes the imaging module according to the first aspect.

A catheter according to one or more embodiments of the present invention includes: the imaging module according to the first aspect; a tube that surrounds the imaging module and has an insulation property; and a channel provided in the tube.

As described above, according to the above-mentioned embodiments, it is possible to provide an imaging module that has a small diameter and can achieve an endoscope obtaining sufficient illuminance without using a light guide fiber, an endoscope including the imaging module, and a catheter including the endoscope.

DETAILED DESCRIPTION

Figure 1A:
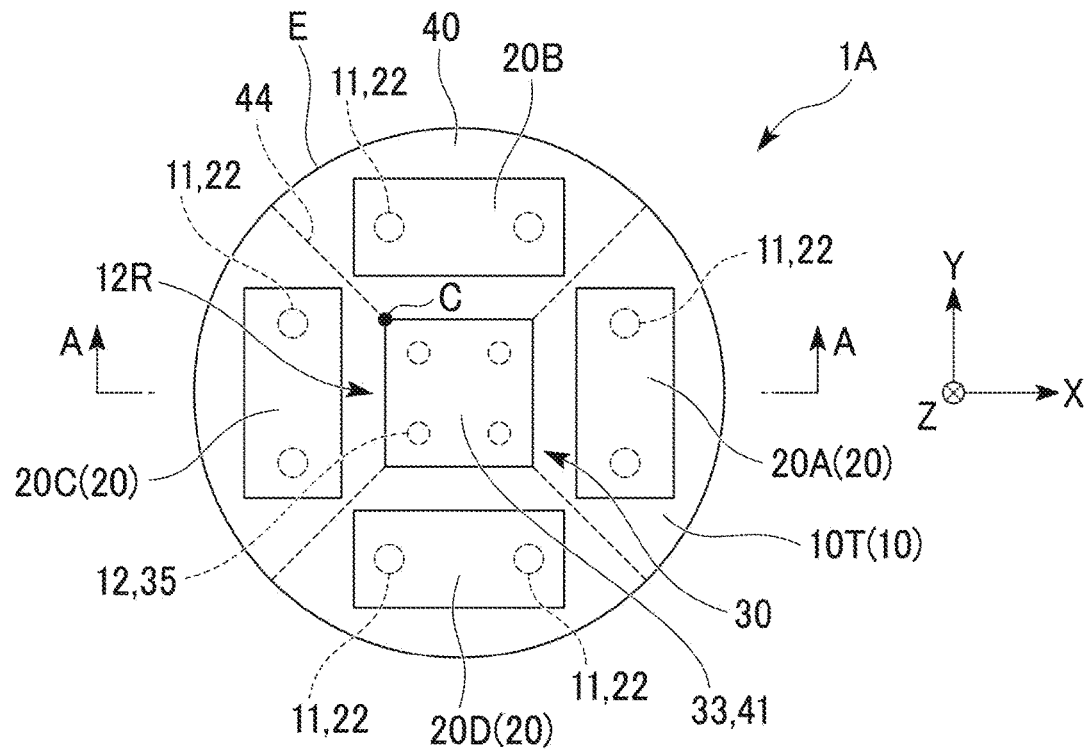
FIG. 1A is a plan view showing a relevant part of an imaging module according to one or more embodiments of the present invention.

Hereinafter, one or more embodiments of the present invention will be described with reference to drawings.

In the drawings showing embodiments of the invention, in order for the respective components to be of understandable size in the drawings, the dimensions and the proportions of the components are modified as needed compared with the real components.

Imaging Module 1A

Figure 1B:
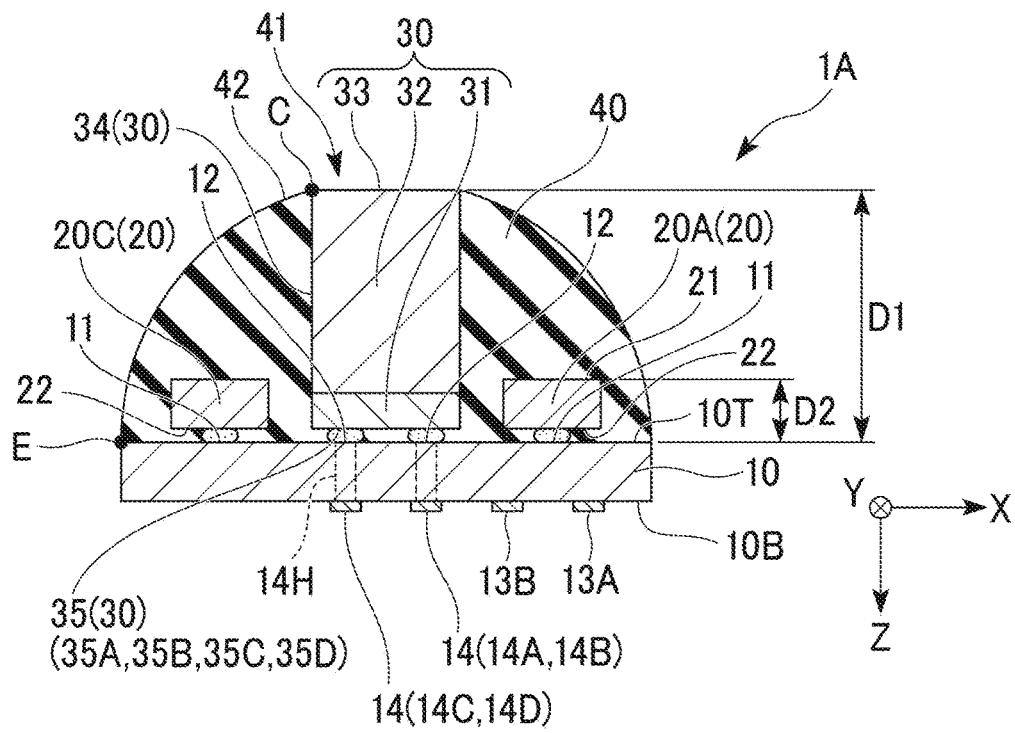
FIG. 1B is a view showing a relevant part of the imaging module according to one or more embodiments of the present invention and is a cross-sectional view taken along the line A-A shown in FIG. 1A.

FIGS. 1A and 1B are views showing a relevant part of an imaging module 1A according to one or more embodiments of the present invention. FIG. 1A is a plan view as seen in a vertical direction of the imaging module 1A (Z-direction). FIG. 1B is a cross-sectional view taken along the line A-A shown in FIG. 1A and is a view as seen in a direction parallel to a support substrate 10 constituting the imaging module 1A.

The imaging module 1A includes the support substrate 10, light-emitting diodes 20 (planar light emitter), a solid-state image sensing device 30, and a cover member 40.

Support Substrate 10

The support substrate 10 has an upper face 10T (first surface) and a lower face 10B (second surface) that is located on the opposite side of the upper face 10T. As a constituent material of the support substrate 10, a constituent material of a printed circuit board (PCB, Printed Circuit Board) such as epoxy glass is used.

A plurality of first mounting terminals 11 and a plurality of second mounting terminals 12 disposed adjacent to the first mounting terminals 11 are provided on the upper face 10T. In one or more embodiments, the plurality of first mounting terminals 11 are disposed so as to surround the periphery of a formation region 12R of the second mounting terminals 12.

As described below, the light-emitting diode 20 is mounted on the first mounting terminals 11, and the solid-state image sensing device 30 is mounted on the second mounting terminals 12.

An external positive terminal 13A (first external terminal), an external negative terminal 13B (first external terminal), and a plurality of imaging external terminals 14 (second external terminal) are provided on the lower face 10B. In one or more embodiments, four imaging external terminals 14 (14A, 14B, 14C, 14D) corresponding to four image-sensing terminals 35 are provided on the lower face 10B.

In FIG. 1B, the two imaging external terminals 14A and 14B align in the Y-direction, and the two imaging external terminals 14C and 14D similarly align in the Y-direction.

The external positive terminal 13A and the external negative terminal 13B are electrically connected to the light-emitting diode 20 via the first mounting terminals 11.

The imaging external terminals 14 are electrically connected to the solid-state image sensing device 30 via the second mounting terminals 12.

The external positive terminal 13A, the external negative terminal 13B, and the imaging external terminals 14 are electrically connected to a connector, an outer cable, or the like which will be described later.

For example, lower surface wirings (wiring pattern) which are not shown in the drawings are formed on the lower face 10B, and the first mounting terminals 11 are connected to the lower surface wirings via through conductors that are not shown in the drawings and penetrate through the support substrate 10. Additionally, the external positive terminal 13A and the external negative terminal 13B are connected to the lower surface wirings. That is, the external positive terminal 13A and the external negative terminal 13B are electrically connected to the first mounting terminals 11 via the through conductors and the lower surface wirings.

In the configuration in which the light-emitting diodes 20 are mounted on the first mounting terminals 11, the external positive terminal 13A and the external negative terminal 13B supply electric power to the light-emitting diodes 20.

Note that, the wiring structure between the external negative terminal 13B and the first mounting terminals 11, and, the wiring structure between the external positive terminal 13A and the first mounting terminals 11 are not limited to the configuration including the lower surface wirings. In the case where the support substrate 10 is a multi-layered substrate in which wiring layers and an insulating layer are stacked in layers, a wiring that connects the external positive terminal 13A to the first mounting terminal 11 or a wiring that connects the external negative terminal 13B to the first mounting terminal 11 may be provided inside the multi-layered substrate.

The imaging external terminals 14 are electrically connected to the second mounting terminals 12 via through conductors 14H that penetrate through the support substrate 10.

As described below, in the configuration in which the solid-state image sensing device 30 is mounted on the second mounting terminals 12, the imaging external terminals 14 supply electric power from a power supply line which is not shown in the drawings to the solid-state image sensing device 30, and output the image signals output from the solid-state image sensing device 30 to an external output wiring which is not shown in the drawings.

Light-Emitting Diode 20

The light-emitting diode 20 includes: a light-emitting face 21; and light-emitter terminals 22 connected to the first mounting terminals 11 with solder interposed therebetween. When seen in a plan view, the light-emitting diode 20 (light-emitting face 21) is formed in a rectangular shape.

In one or more embodiments, for example, a surface-mounted light emitting diode is applied as the light-emitting diode 20. Consequently, light having straightness can be emitted from the light-emitting face 21, and it is possible to ensure sufficient illuminance.

As shown in FIG. 1A, the four light-emitting diodes 20A, 20B, 20C, and 20D face the four sides of the solid-state image sensing device 30 and are arranged so as to surround the periphery of the solid-state image sensing device 30 in parallel to the solid-state image sensing device 30. In one or more embodiments, the four light-emitting diodes 20A, 20B, 20C, and 20D are series-connected to the external positive terminal 13A and the external negative terminal 13B. Particularly, electrical current supplied to the external positive terminal 13A flows toward the external negative terminal 13B in order of the light-emitting diode 20A, the light-emitting diode 20B, the light-emitting diode 20C, and the light-emitting diode 20D.

In other cases, as long as straightness of light is reliably obtained, it is not limited to a surface-mounted light emitting diode, and a planar light emitter having the other configuration may be applied to one or more embodiments of the present invention.

Moreover, as an electrical circuit that supplies electric power to the four light-emitting diodes, it is not limited to the aforementioned series connection. Parallel connection may be adopted such that one end of the light-emitter terminal 22 is electrically connected to the external positive terminal 13A and the other end of the light-emitter terminal 22 is connected to the external negative terminal 13B for each of the light-emitting diodes. In order to avoid the wiring pathway from being complicated, series connection may be used.

Furthermore, as described hereinbelow, a controller that controls light emission of each of the light-emitting diodes may be provided on the support substrate 10.

Solid-State Image Sensing Device 30

The solid-state image sensing device 30 is an image-sensing device that is integrated with a rectangular-shaped lens and is, for example, an image-sensing device using WLO (Wafer Leveled Optics).

Specifically, the solid-state image sensing device 30 includes an imaging sensor 31, a glass member 32 that is connected to and provided on the imaging sensor 31, a light-incident surface 33 that is located at the upper face of the glass member 32, a light-shielding portion 34 that coats the periphery of the solid-state image sensing device 30, and four image-sensing terminals 35 (35A, 35B, 35C, 35D) that are provided on the lower face of the solid-state image sensing device 30.

The solid-state image sensing device 30 is disposed adjacent to the four light-emitting diodes 20. In FIG. 1B, the two image-sensing terminals 35A and 35B align in the Y-direction, and the two image-sensing terminals 35C and 35D similarly align in the Y-direction.

An imaging object is irradiated with light emitted from the light-emitting face 21 of the light-emitting diode 20, the reflected light from the imaging object is incident to the light-incident surface 33 of the solid-state image sensing device 30, passes through the glass member 32, and is incident to the imaging sensor 31. Accordingly, the solid-state image sensing device 30 captures an image of the imaging object.

As the imaging sensor 31, for example, a CMOS (complementary metal oxide semiconductor) may be used. In other cases, as a configuration of the imaging sensor 31, it is not limited to the CMOS, the other device may be used.

The light-incident surface 33 is formed in a quadrangular shape in plan view. The light-incident surface 33 is not covered with the cover member 40, but is exposed, and forms the front-end of the imaging module 1A.

When seen in a cross-sectional view in a direction perpendicular to the light-incident surface 33, the distance D1 from the upper face 10T to the light-incident surface 33 is greater than the distance D2 from the upper face 10T to the light-emitting face 21.

The light-shielding portion 34 prevents the light that is emitted from the light-emitting diodes 20 located next to the solid-state image sensing device 30 from being incident to the inside thereof through the side face of the solid-state image sensing device 30. Particularly, the periphery of the glass member 32 (except for light-incident surface 33) is coated with a light-shielding material that blocks light from the light-emitting diode 20, and the light-shielding portion 34 is thereby formed. The light-shielding portion 34 is not limited to a coating film, and the light-shielding portion 34 may be a member that exhibits a light shielding effect. The light-shielding portion 34 surrounds the glass member 32.

The image-sensing terminals 35 are connected to the second mounting terminals 12 via solder. That is, the solid-state image sensing device 30 is connected to the second mounting terminals 12 on the support substrate 10.

Cover Member 40

The cover member 40 is provided on the upper face 10T of the support substrate 10, is formed of a transparent resin, adhesive, or the like, and covers over the four light-emitting diodes 20 (20A, 20B, 20C, 20D) and the solid-state image sensing device 30.

For example, in the case of using a transparent resin as the cover member 40, the transparent resin having flowability is supplied on the upper face 10T of the support substrate 10, the resin is cured by a publicly known curing method such as heat-curing or ultraviolet curing, and it is possible to form the cover member 40. As long as sufficient transparency is obtained for a transparent resin, a material used to form the transparent resin is not limited.

Additionally, in the case of using adhesive as the cover member 40, acrylic transparent adhesive, a transparent UV curable resin, or the like is used. As long as a transparent adhesive is used, a constituent material of the cover member 40 is not limited.

The cover member 40 includes: an exposed area 41 at which the light-incident surface 33 is exposed; and an outer surface 42.

When seen in a cross-sectional view, the outer surface 42 extends from the corner C (outer-periphery) of the light-incident surface 33 to the edge E of the support substrate 10. Particularly, the outer surface 42 has a curved surface (fillet shape) that bulges (protrusion) toward the outside from the straight line connecting the corner C and the edge E in the cross-sectional view. That is, the cover member 40 has a dome shape (hemispherical body). In the case of applying the imaging module 1A to an endoscope for observation of an inside of a living body, since the surface shape of the cover member 40 is the hemispherical body, it is easy to be inserted into the inside of the living body, and mucosa of the living body can be protected.

In the example shown in FIG. 1A, on the surface of the cover member 40, the curved surface of the outer surface 42 is formed in the directions radially extending from the center of the light-incident surface 33 along the four ridge lines 44 reaching the edge E from the corner C. In other words, the cover member 40 has the shape such that the cross-sectional area of the cover member 40 in the directions orthogonal to the Z-direction gradually increases in the direction from the upper face 10T to the light-incident surface 33.

As an example, the configuration in which the ridge lines 44 are formed on the outer surface 42 (surface) of the cover member 40 is shown in one or more embodiments; however, the ridge lines 44 are not necessarily required to be formed. A spherical surface on which the ridge lines 44 are not formed may be formed on the outer surface 42.

Since the light-incident surface 33 is exposed at the exposed area 41, the reflected light from the imaging object enters the light-incident surface 33 without passing through the transparent material constituting the cover member 40.

A curvature of the outer surface 42 is appropriately determined in consideration of a lens effect, light diffusion effect, or the like which is obtained by the cover member 40.

Particularly, although the cover member 40 is formed by curing a transparent resin supplied to the upper face 10T of the support substrate 10 in the above-mentioned embodiments, the invention is not limited to this configuration.

For example, the cover member 40 may be configured by: preliminarily shaping a transparent resin cap including a through hole corresponding to the shape of the solid-state image sensing device 30 and a recessed portion corresponding to the shape of the light-emitting diode 20; and disposing the resin cap (molded product) on the support substrate 10 as shown in FIG. 1B. In this case, as the transparent resin forming the resin cap, transparent plastic materials such as PC (polycarbonate), acrylic resin, or the like are used.

Furthermore, the cover member 40 may be configured by combination of a transparent resin cap and transparent adhesive. In this case, firstly, a transparent resin cap including a through hole corresponding to the shape of the solid-state image sensing device 30 is prepared in advance. Next, adhesive is supplied to the upper face 10T so as to coat the light-emitting diode 20 mounted on the support substrate 10. Thereafter, the resin cap is disposed on the adhesive so as to fit the solid-state image sensing device 30 into the through hole, and the adhesive is cured. Consequently, the structure shown in FIG. 1B is obtained.

Note that, in the case where the adhesive is formed of a UV curable resin, it is possible to cure the adhesive by irradiating the adhesive through the resin cap with UV light emitted from a UV light source provided outside the resin cap.

In the imaging module 1A according to one or more embodiments, since the solid-state image sensing device 30 and the light-emitting diode 20 can be disposed on the single support substrate 10, it is possible to achieve miniaturization of the imaging module.

Furthermore, not only the advantage of downsizing the imaging module but also an advantage in that a camera module with illumination can be achieved by packaging the solid-state image sensing device 30 and the light-emitting diode 20 into the single support substrate 10 can be obtained.

Specifically, since a plurality of the rectangular-shaped light-emitting diodes 20 are arranged so as to be in parallel to the solid-state image sensing device 30 at the periphery of the solid-state image sensing device 30 formed in a quadrangular shape, it is possible to obtain an optimal design condition in terms of miniaturization of components to be mounted on the support substrate 10.

Since the cover member 40 formed of the transparent material is provided on the support substrate 10, it is possible to protect the light-emitting diode 20 and the solid-state image sensing device 30. The light emitted from the light-emitting diodes 20 can be guided into the outside of the imaging module 1A and light can be emitted.

Since the cover member 40 has the exposed area 41, the imaging object is illuminated by the light-emitting diode 20, and the reflected light from the imaging object enters the light-incident surface 33 without passing through the cover member 40. For this reason, the solid-state image sensing device 30 can obtain an image of the imaging object as a picture. Because of this, degradation in image quality due to transmissivity or refraction index of the transparent material can be prevented.

Since the imaging module 1A does not use a light guide fiber, it is possible to cause the light-emitting diode 20 to emit light at the position close to the imaging object, and the imaging object can be illuminated with the light emitted from the light-emitting diode 20. As a result, it is possible to obtain sufficient illuminance.

Different from a conventional imaging module, since a light guide fiber is not used, it is not necessary to handle the light guide fiber, and issues of breakage due to bending of the optical fiber, an increase in size due to an increase in the numbers of the optical fibers, or the like do not occur.

MODIFIED EXAMPLES

Next, modified examples 1 to 7 of one or more embodiments will be described.

In the modified examples 1 to 7 described below, identical symbols are used for the elements which are identical to those of one or more embodiments, and the explanations thereof are omitted or simplified here.

Figure 2A:
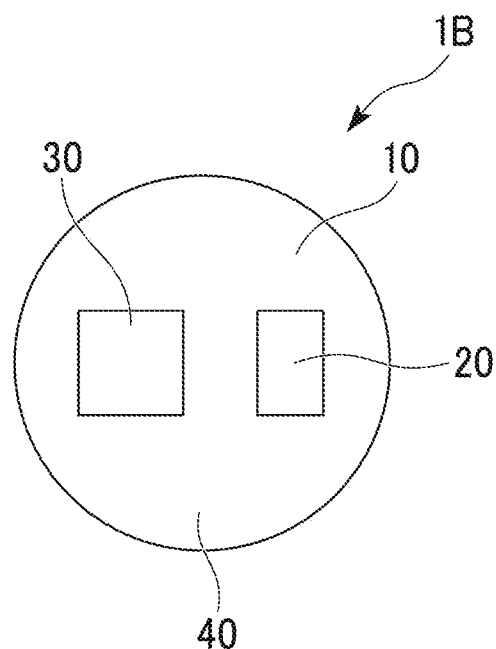
FIG. 2A is a plan view showing a modified example 1 of the imaging module according to one or more embodiments of the present invention.
Figure 2B:
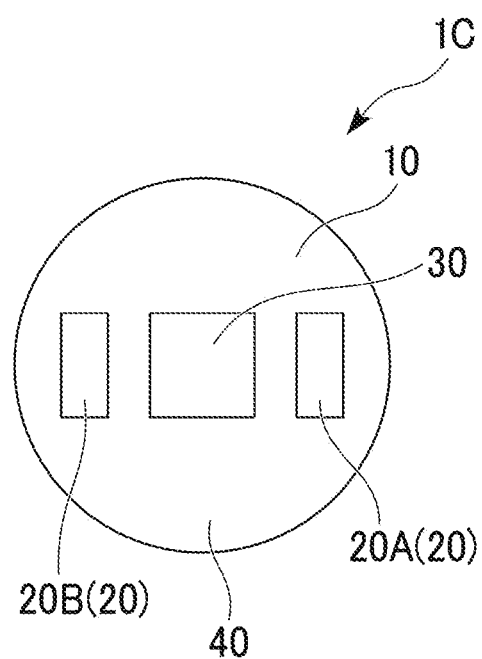
FIG. 2B is a plan view showing a modified example 2 of the imaging module according to one or more embodiments of the present invention.
Figure 2C:
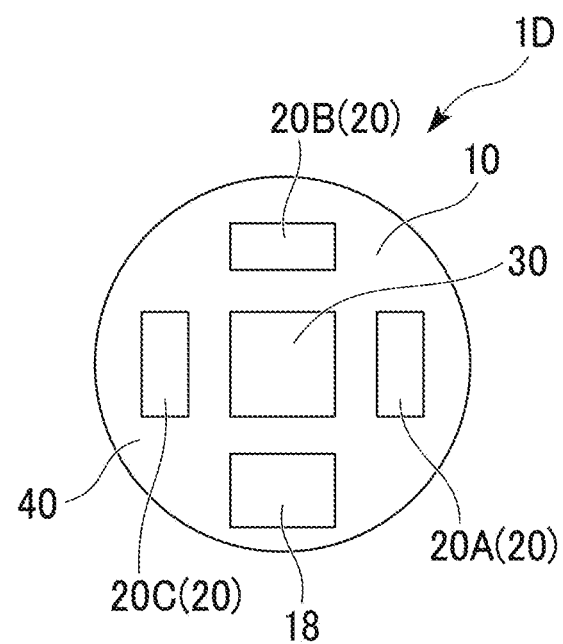
FIG. 2C is a plan view showing a modified example 3 of the imaging module according to one or more embodiments of the present invention.

FIGS. 2A to 2C are plan views showing the modified examples of the imaging module according to one or more embodiments of the present invention. FIG. 2A is a plan view showing a modified example 1. FIG. 2B is a plan view showing a modified example 2. FIG. 2C is a plan view showing a modified example 3.

Figure 3A:
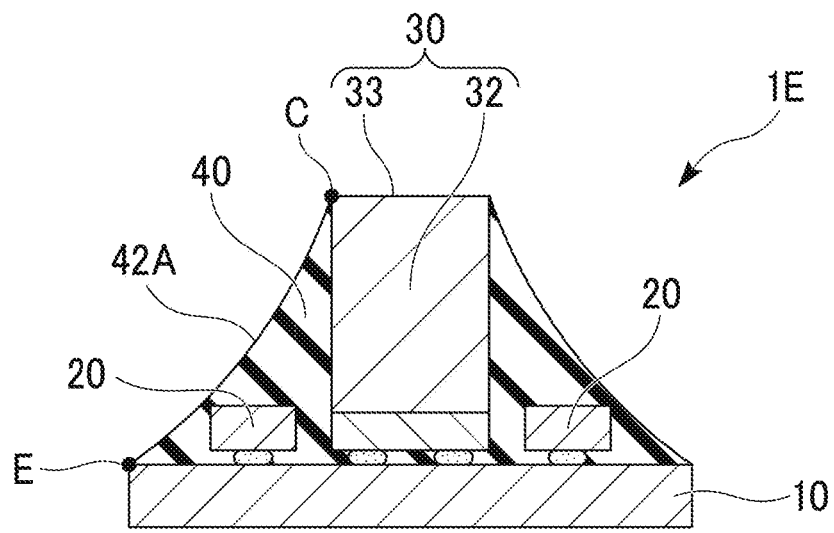
FIG. 3A is a plan view showing a modified example 4 of the imaging module according to one or more embodiments of the present invention.
Figure 3B:
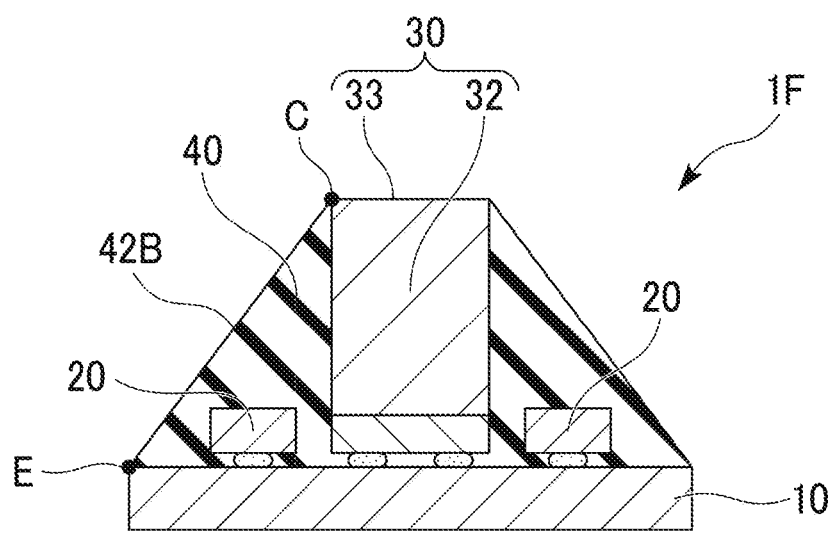
FIG. 3B is a plan view showing a modified example 5 of the imaging module according to one or more embodiments of the present invention.

FIGS. 3A and 3B are cross-sectional views showing the modified examples the imaging module according to one or more embodiments of the present invention. FIG. 3A is a cross-sectional view showing a modified example 4. FIG. 3B is a cross-sectional view showing a modified example 5.

Modified Example 1

Although the configuration in which the four light-emitting diodes 20 are mounted on the support substrate 10 is described in the above-described embodiments, the solid-state image sensing device 30 has only to be disposed next to one or more light-emitting diodes 20.

For example, as shown in FIG. 2A, an imaging module 1B includes: one light-emitting diode 20 that is disposed on the support substrate 10; and the solid-state image sensing device 30 that is disposed on the support substrate 10 and is disposed adjacent to the light-emitting diode 20.

In the imaging module 1B according to the modified example 1, since one light-emitting diode 20 is provided on the support substrate 10, it is possible to reduce the mounting area on which the light-emitting diode 20 is mounted on the support substrate 10. Consequently, it is possible to achieve miniaturization of the imaging module 1B to be smaller than the configuration including a plurality of light-emitting diodes.

Modified Example 2

As shown in FIG. 2B, an imaging module 1C includes: two light-emitting diodes 20 (20A, 20B) that are disposed on the support substrate 10; and the solid-state image sensing device 30 that is disposed on the support substrate 10 and is disposed adjacent to the light-emitting diode 20.

In particular, the light-emitting diodes 20 are disposed at the right and left of the solid-state image sensing device 30, in other words, the solid-state image sensing device 30 is disposed between the light-emitting diodes 20A and 20B. That is, the light-emitting diodes 20A and 20B are arranged so as to surround the solid-state image sensing device 30.

In the imaging module 1C according to the modified example 2, since the two light-emitting diodes 20 are provided on the support substrate 10, the mounting area of the light-emitting diodes is smaller than the configuration including three or more light-emitting diodes, it is possible to achieve miniaturization of the imaging module 1C, and it is possible to ensure illuminance higher than the case where the number of the light-emitting diodes is one.

Modified Example 3

As shown in FIG. 2C, an imaging module 1D includes: three light-emitting diodes 20 (20A, 20B, 20C) that are disposed on the support substrate 10; and the solid-state image sensing device 30 that is disposed on the support substrate 10 and is disposed adjacent to the light-emitting diode 20.

Particularly, the light-emitting diodes 20A, 20B, and 20C are arranged so as to face the three sides of the solid-state image sensing device 30. That is, the light-emitting diodes 20A, 20B, and 20C are arranged so as to surround the solid-state image sensing device 30. The position facing the remaining one side of the solid-state image sensing device 30 is a mounting region 18.

A functional element (functional device), for example, a capacitor, IC chip, or the like, that is, a component different from the solid-state image sensing device 30 and the light-emitting diode 20 is mounted on the mounting region 18.

In the imaging module 1D according to the modified example 3, since the mounting region 18 is provided on the support substrate 10, it is possible to achieve a highly-functional imaging module 1D having a function other than the light emission function and the image-sensing function.

In the case where a capacitor is mounted on the mounting region 18, the capacitor is electrically connected to, for example, the image-sensing terminal 35 of the solid-state image sensing device 30.

In the case where an IC chip is mounted on the mounting region 18, the IC chip may be, for example, a driver driving the light-emitting diode 20. An IC chip having other functions may be provided on the mounting region 18.

Modified Example 4

As shown in FIG. 3A, an imaging module 1E is different from the aforementioned embodiments in outer surface shape of the cover member 40.

An outer surface 42A reaches the edge E of the support substrate 10 from the corner C of the light-incident surface 33. The outer surface 42A has a curved surface (fillet shape) that is depressed inwardly from the straight line connecting the corner C and the edge E when seen in a cross-sectional view.

Modified Example 5

As shown in FIG. 3B, in an imaging module 1F, an outer surface 42B of the cover member 40 has the straight line connecting the corner C and the edge E when seen in a cross-sectional view. That is, in the three-dimensional structure, the cover member 40 has a circular truncated cone shape.

The shape of the outer surface 42 is not limited to the configuration shown in the aforementioned embodiments and the modified examples 4 and 5.

For example, the outer surface 42 may have a recessed and projected surface which is formed of combination of: a projected surface bulging toward the outside from the straight line connecting the corner C and the edge E; and a recessed surface being depressed inwardly from the straight line connecting the corner C and the edge E. Moreover, the outer surface 42A shown in the modified example 4 may have the recessed and projected surface, and the outer surface 42B shown in the modified example 5 may have the recessed and projected surface.

Furthermore, as the ridge lines 44 directed from the corner C to the edge E, for example, the cover member 40 may be formed such that spiral lines are drawn on the outer surfaces 42, 42A, and 42B.

In one or more embodiments and the modified examples, the configuration in which the light-emitting diodes 20 are arranged at the positions facing the four sides of the solid-state image sensing device 30 is described; however, the invention is not limited to this configuration.

A plurality of the light-emitting diodes 20 may be arranged along the circumference of the support substrate.

Modified Example 6

Although the cover member 40 includes the exposed area 41 at which the light-incident surface 33 is exposed in one or more embodiments and the modified examples 4 and 5, the invention is not limited to the above-described configuration.

For example, the cover member 40 may include a coating portion that coats the light-incident surface 33. In this case, the coating portion functions as, for example, a protector that protects the light-incident surface 33.

Additionally, regarding the imaging module in the endoscope for observation of an inside of a living body, in the case where there is a concern that the light-incident surface 33 of the imaging module damages the living body, the coating portion that coats the light-incident surface 33 functions as a protector that protects the living body.

Note that, the meaning of "the coating portion that coats the light-incident surface" is not limited to coating of the entire surface of the light-incident surface 33 but includes coating of part of the light-incident surface 33.

For example, the light-incident surface 33 may be partially exposed at the center region of the light-incident surface 33 (the region except for the corner or the edge represented by reference letter C shown in FIGS. 1A, 1B, 3A, and 3B), and the corner or the edge (part of the light-incident surface) of the light-incident surface 33 represented by reference letter C may be covered with the coating portion.

In this case, the reflected light from the imaging object enters the center region of the light-incident surface 33 without passing through the transparent material. Consequently, an image of the imaging object can be obtained as a picture, and degradation in image quality due to transmissivity or refraction index of the transparent material can be prevented. Furthermore, since the corner or the edge of the light-incident surface 33 represented by reference letter C is covered with the coating portion, the solid-state image sensing device 30 is the protected by the coating portion, and breakage of the solid-state image sensing device 30 can be prevented.

Moreover, if there is a concern that the solid-state image sensing device 30 damages the inside of the living body at the portion represented by reference letter C, the configuration can be adopted in which the corner or the edge (part of the light-incident surface) of the light-incident surface 33 represented by reference letter C is coated with the coating portion and the light-incident surface 33 is partially exposed at the center region of the light-incident surface 33.

In this case, degradation in image quality can be prevented, and the living body can be protected by the coating portion.

Modified Example 7

Although the case where the curving line or the straight line connecting the corner C and the edge E is formed in cross-section of the cover member 40 is described in the above-mentioned embodiments and the modified examples 4 and 5, the invention is not limited to this configuration.

The meaning of "an outer surface that reaches an edge E of the support substrate from an outer-periphery (corner C) of the light-incident surface in the cross-sectional view" includes the configuration in which the intermediate portion located between the corner C and the edge E is defined as the starting point, a curving line or a straight line is formed to be directed from the intermediate portion toward the corner C, and a curving line or a straight line is formed to be directed from the intermediate portion toward the edge E.

Imaging Module 1G

Figure 4A:
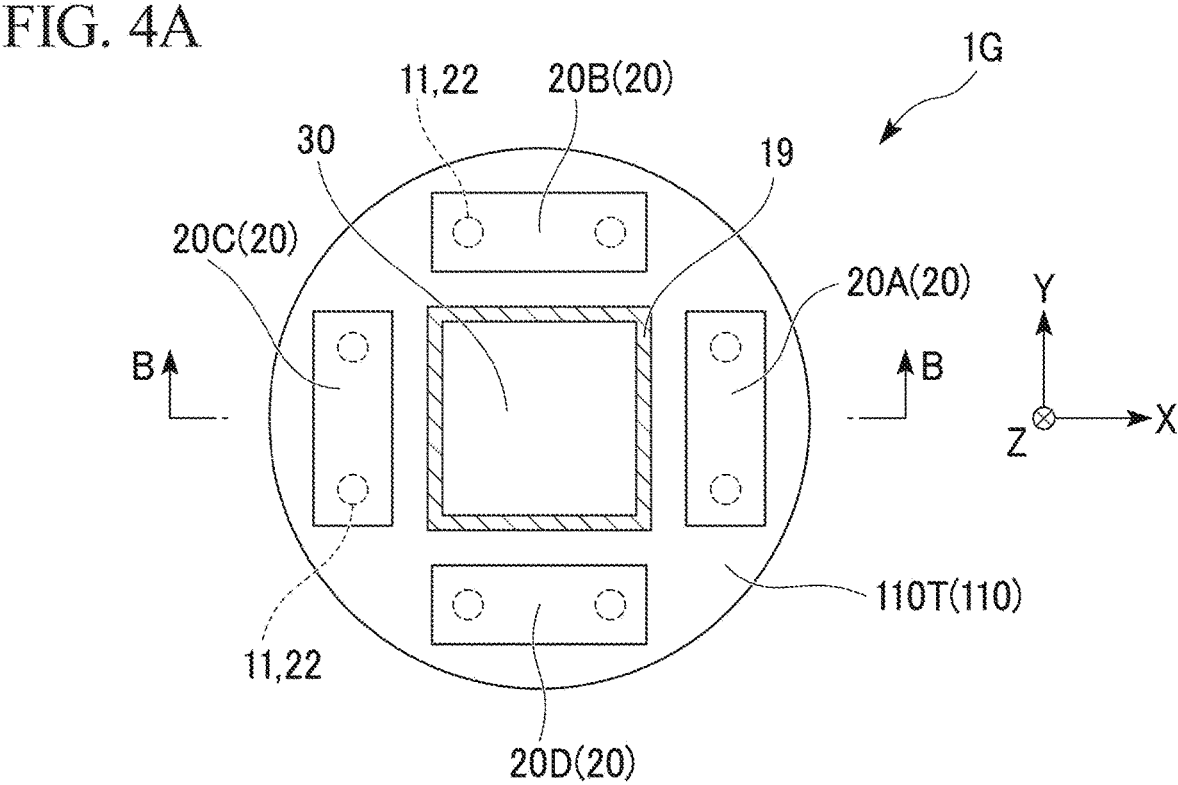
FIG. 4A is a plan view showing a relevant part of an imaging module according to one or more embodiments of the present invention.
Figure 4B:
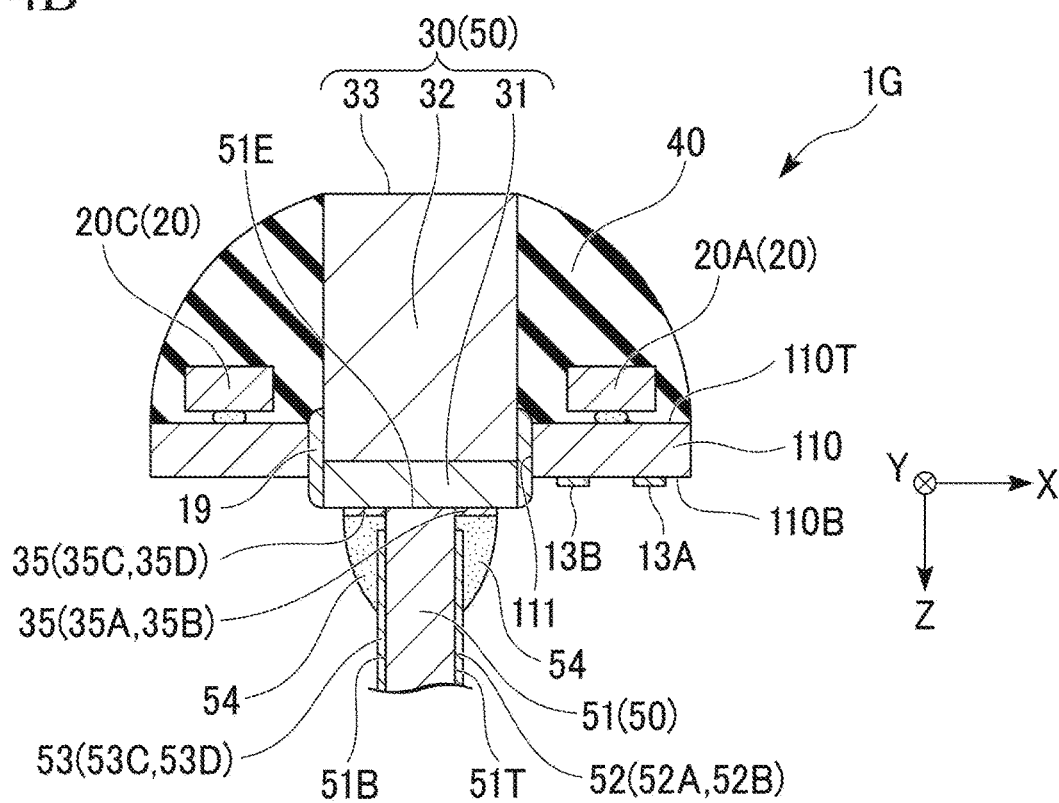
FIG. 4B is a view showing a relevant part of the imaging module according to one or more embodiments of the present invention and is a cross-sectional view taken along the line B-B shown in FIG. 4A.

FIGS. 4A and 4B are views showing a relevant part of an imaging module 1G according to one or more embodiments. FIG. 4A is a plan view as seen in the vertical direction of the imaging module 1G (Z-direction). FIG. 4B is a cross-sectional view taken along the line B-B shown in FIG. 4A and is a view as seen in a direction (Y-direction) parallel to the imaging module 1G.

In one or more embodiments described below, identical symbols are used for the elements which are identical to those of the above-mentioned embodiments and the modified examples, and the explanations thereof are omitted or simplified here.

In one or more embodiments, the imaging module 1G includes a support substrate 110 and an imaging unit 50.

Support Substrate 110

The support substrate 110 includes a through hole 111 that extends from a lower face 110B (second surface) to an upper face 110T (first surface) and penetrates through the support substrate 110. The through hole 111 is located at the center of the support substrate 110, that is, adjacent to the first mounting terminals 11.

The second mounting terminals 12 are not formed on the upper face 110T, but only a plurality of the first mounting terminals 11 are formed on the upper face 110T. Similarly, the imaging external terminals 14 are not formed on the lower face 110B, but only the external positive terminal 13A and the external negative terminal 13B are formed on the lower face 110B.

The electric connection structure between the first mounting terminals 11, the external positive terminal 13A, and the external negative terminal 13B, and the light-emitting diodes 20 (20A, 20B, 20C, 20D) is the same as that of the above-described embodiments.

Imaging Unit 50

The imaging unit 50 is a body separate from the support substrate 110, is inserted into the through hole 111 of the support substrate 110, and is fixed by a fixing member 19 such as resin. The aforementioned solid-state image sensing device 30 is electrically connected to the imaging unit 50, in this state, the solid-state image sensing device 30 is disposed adjacent to the first mounting terminals 11.

The imaging unit 50 includes a base 51. The base 51 includes a base upper face 51T and a base lower face 51B. First electrical wires 52 (52A, 52B) are formed on the base upper face 51T, and second electrical wires 53 (53C, 53D) are formed on the base lower face 51B. In FIG. 4B, the two first electrical wires 52A and 52B align in the Y-direction, and the two second electrical wires 53C and 53D similarly align in the Y-direction.

The end face 51E of the base 51 is fixed at the lower face of the solid-state image sensing device 30, in this state, the image-sensing terminals 35A and 35B are electrically connected to the first electrical wires 52A and 52B, respectively, via solder 54. The image-sensing terminals 35C and 35D are electrically connected to the second electrical wires 53C and 53D, respectively, via the solder 54. A specific wiring structure of the imaging unit 50 will be described later with reference to FIG. 7.

In the configuration in which the imaging unit 50 is fixed to the through hole 111 of the support substrate 110, the first electrical wires 52A and 52B and the second electrical wires 53C and 53D supply electric power from a power supply line which is not shown in the drawings to the solid-state image sensing device 30, and output the image signals output from the solid-state image sensing device 30 to an external output wiring which is not shown in the drawings.

In the imaging module 1G according to one or more embodiments, as the imaging unit 50 is used which is a body separate from the support substrate 110, it is not necessary to arrange the solid-state image sensing device 30 and the light-emitting diode 20 on the same support substrate. That is, after the base 51 and the solid-state image sensing device 30 are connected and the imaging unit 50 is thereby obtained, only by fixing the imaging unit 50 to the through hole 111, a downsized imaging module can be achieved. Accordingly, complicated mounting steps with respect to the support substrate can be omitted.

Furthermore, it is possible to independently manufacture and inspect the imaging unit 50 and the support substrate 110 on which the light-emitting diode 20 is mounted. That is, before the imaging unit 50 is fixed to the through hole 111 of the support substrate 110, inspection can be carried out with respect to each of the imaging unit 50 and the support substrate 110, and it is possible to determine whether or not it is a non-defective product. As a result, it is possible to manufacture the imaging module 1G by combination of the imaging unit 50 and the support substrate 110 provided that each of them is determined as a non-defective product in the inspection. Particularly, before assembling the imaging unit 50 and the support substrate 110 into one body, it is possible to prevent a defective component from being used for an imaging module.

In contrast, regarding the support substrate on which the light-emitting diode and the solid-state image sensing device are collectively mounted, the inspection is carried out after the light-emitting diode and the solid-state image sensing device are mounted on the support substrate, and it is determined whether or not the packaged structure (a completed product of the imaging module, or an intermediate structure before the cover member is molded) is a non-defective product.

For example, in the case where one of the light-emitting diode and the solid-state image sensing device is a defective product, regardless of whether or not the other is a non-defective product, it is determined that the packaged structure is defective. Because of this, even in the case where the packaged structure includes a non-defective product, the packaged structure has to be discarded, and therefore there is an issue in that a non-defective product constituting the packaged structure is wasted.

In contrast, in the imaging module 1G according to one or more embodiments, before manufacturing the imaging module 1G by assembling the imaging unit 50 and the support substrate 110 into one body, since it is possible to determine whether or not the imaging unit 50 and the support substrate 110 is a non-defective product, the issue in that the non-defective product constituting the imaging module is wasted does not occur.

Moreover, similar to the aforementioned embodiments, it is possible to cause the light-emitting diode 20 to emit light at the position close to the imaging object, and it is possible to illuminate the imaging object with sufficient illuminance using the light emitted from the light-emitting diode 20. Furthermore, unlike a conventional imaging module, issues of breakage due to bending of an optical fiber, an increase in size due to an increase in the numbers of the optical fibers, or the like do not occur.

Imaging Module 1H

Figure 5:
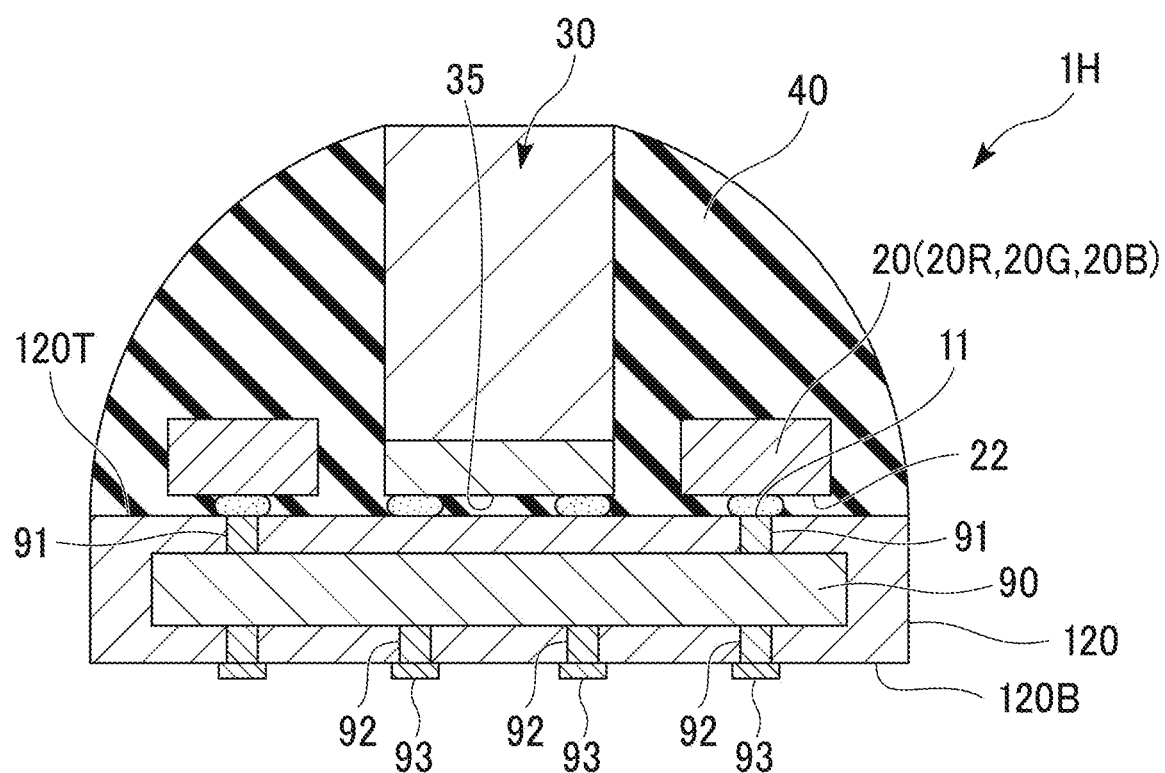
FIG. 5 is a view showing a relevant part of an imaging module according to one or more embodiments of the present invention and is a cross-sectional view for explanation of a schematic configuration of a support substrate including a controller.

FIG. 5 is a view showing a relevant part of an imaging module 1H according to one or more embodiments of the present invention and is a cross-sectional view for explanation of a schematic configuration of a support substrate 120 including a controller 90.

In one or more embodiments described below, identical symbols are used for the elements which are identical to those of the above-mentioned embodiments, and the explanations thereof are omitted or simplified here.

In one or more embodiments, the imaging module 1H includes the support substrate 120.

Moreover, in FIG. 5, an electric connection structure between the image-sensing terminals 35 and the imaging external terminals 14 is omitted, and the electric connection structure shown in FIGS. 1A and 1B is applied to the imaging module 1H.

Support Substrate 120

The support substrate 120 includes: the controller 90 that controls light emission of the light-emitting diodes 20 (20A, 20B, 20C, 20D); first control wirings 91 (control wiring) that connect the controller 90 to the first mounting terminals 11; control terminals 93 provided on a lower face 120B (second surface) of the support substrate 120; and second control wirings 92 (control wiring) that connect the controller 90 to the control terminals 93.

In one or more embodiments, the support substrate 120 includes a plurality of the first control wirings 91, a plurality of the second control wirings 92, and a plurality of the control terminals 93.

Signal wirings or power supply wirings which are not shown in the drawings are connected to the control terminals 93. The controller 90 controls light emission of the light-emitting diode 20 in accordance with external signals input to the control terminals 93. As a method of causing the light-emitting diodes 20 to emit light by the controller 90, for example, the following light emission methods are adopted.

Pulsed Light Emission

The controller 90 can cause the four light-emitting diodes 20 to carry out pulsed light emission. In this case, it is possible to illuminate, with pulsed light emitted from the light-emitting diode 20, a vibration body (imaging object, vocal band, or the like) that vibrates at a predetermined frequency. Accordingly, the imaging module 1H can capture an image of an imaging object in a state of vibrating as an image.

RGB Light Modulation

The controller 90 can cause the light-emitting diodes 20 to carry out pulsed light emission with red light (R), green light (G), and blue light (B). In addition, the controller 90 blends the three colors of RGB (color combination) and can illuminate an imaging object with the blended lights. Furthermore, the controller 90 can illuminate an imaging object with only one-colored light of the three colors of RGB.

In this case, a light-emitting diode 20R (20) that emits red light, a light-emitting diode 20G (20) that emits green light, and a light-emitting diode 20B (20) that emits blue light are mounted on the support substrate 120. Moreover, one or more light-emitting diodes that can carry out three-color light modulation of RGB may be mounted on the support substrate 120.

Since the three-color light modulation of RGB is possible by the controller 90, it is possible to illuminate, with light, an imaging object (for example, a portion coated with drug solution, or the like) that exhibits a color with respect to light having a specific wavelength. Consequently, the imaging module 1H can capture, as an image, the imaging object that exhibits a color by irradiation with the light having a specific wavelength.

In other cases, for example, FIG. 5 shows the configuration in which a plurality of the light-emitting diodes 20 (20R, 20G, 20B) are connected to one controller 90; however, the controller 90 may be connected to each of the light-emitting diodes 20.

Additionally, the support substrate 120 is applicable to the above-mentioned imaging module 1G.

For example, FIG. 5 shows the configuration in which the controller 90 is provided inside the support substrate 120; however, the position of the controller 90 is not limited. The controller 90 may be provided on any one of the upper face 120T (first surface) and the lower face 120B of the support substrate 120. For example, the controller 90 may be provided on the mounting region 18 shown in FIG. 2C.

The controller 90 may be an IC chip implanted into the inside of the support substrate 120 and may be a layered circuit provided in a multi-layered substrate in which wiring layers and an insulating layer are stacked in layers.

In one or more embodiments described below, identical symbols are used for the elements which are identical to those of the above-mentioned embodiments and the modified examples, and the explanations thereof are omitted or simplified here.

In the following explanation, in the Z-direction, the direction from a connector 210 to the solid-state image sensing device 30 (left side in FIGS. 6 and 7) may be referred to as "forward" or "front side". The direction from the connector 210 to an outer cable 220 (right side in FIGS. 6 and 7) may be referred to as "rearward" or "back side".

Note that, the endoscopes according to one or more embodiments only have an observation function. In the case where such endoscope is applied to a catheter, it becomes the catheter only having an observation function.

Endoscope 200

Figure 6:
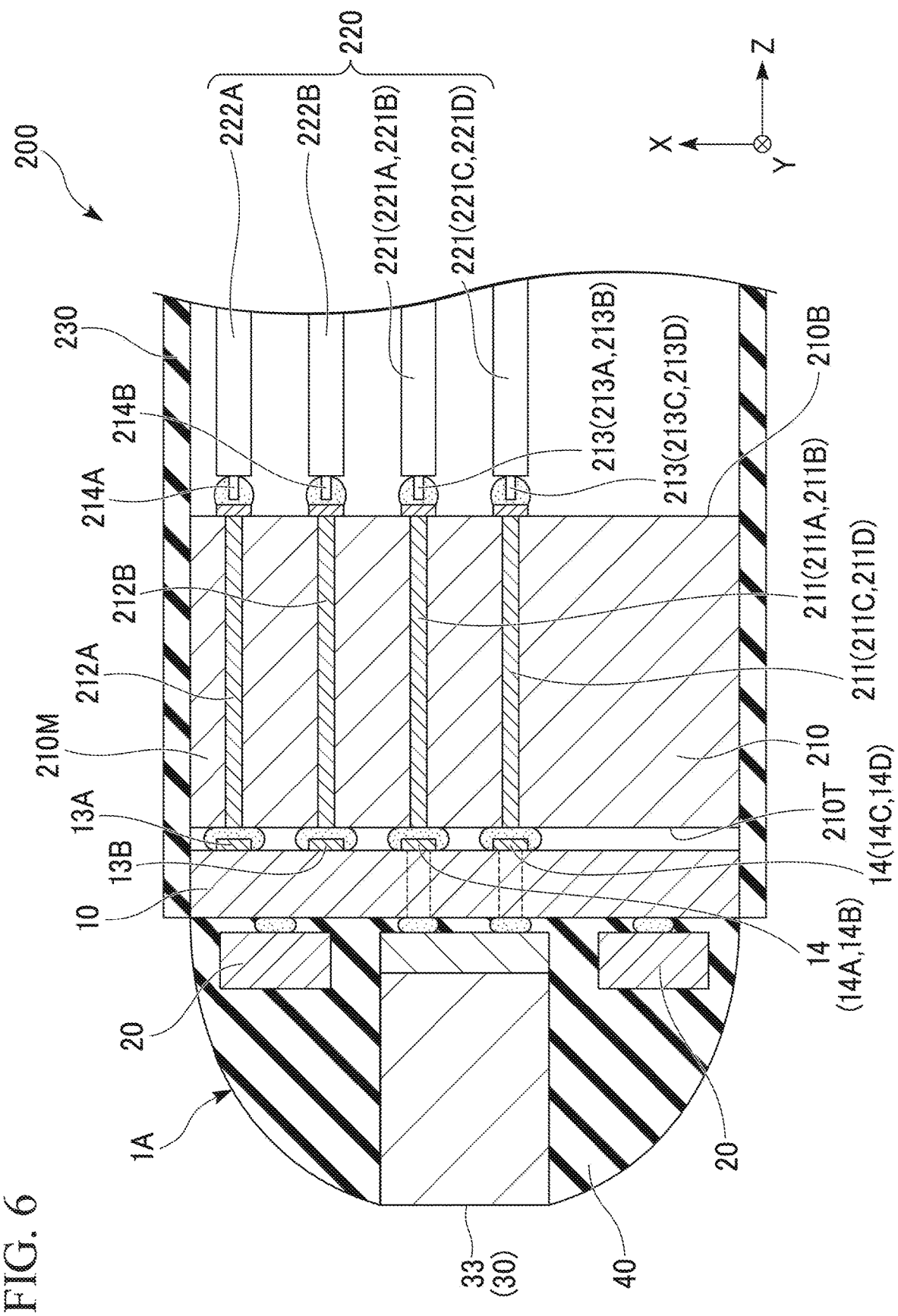
FIG. 6 is a cross-sectional view showing a relevant part of an endoscope according to one or more embodiments of the present invention.

FIG. 6 is a cross-sectional view showing a relevant part of an endoscope 200 according to one or more embodiments of the present invention.

The endoscope 200 includes: the above-mentioned imaging module 1A; the connector 210; the outer cable 220; and an insulating tube 230.

Connector 210

The connector 210 is positioned between the solid-state image sensing device 30 and the outer cable 220.

The connector 210 includes: a main body 230M formed of an insulating member; implanted conductors 211A and 211B (first implanted conductor); implanted conductors 211C and 211D (second implanted conductor); and implanted conductors 212A and 212B (third implanted conductor). The above-described implanted conductors are provided inside the main body 230M and extend in the Z-direction.

In FIG. 6, the two implanted conductors 211A and 211B align in the Y-direction, and the two implanted conductors 211C and 211D similarly align in the Y-direction.

On an upper end face 210T of the connector 210, ends (connection pad) of the implanted conductors 211A, 211B, 211C, 211D, 212A, and 212B face the imaging module 1A.

The four imaging external terminals 14A, 14B, 14C, and 14D are electrically connected to the implanted conductors 211A, 211B, 211C, and 211D via solder, respectively.

The external positive terminal 13A and the external negative terminal 13B are electrically connected to the implanted conductors 212A and 212B via solder, respectively.

Outer Cable 220

The outer cable 220 includes four image-sensor wirings 221 (221A, 221B, 221C, and 221D) and two light-emitting diode wirings 222A and 222B, that is, is configured of six cables.

The image-sensor wirings 221A, 221B, 221C, and 221D include electrical wires 213A, 213B, 213C, and 213D, respectively. The light-emitting diode wirings 222A and 222B include electrical wires 214A and 214B, respectively.

On a lower end face 210B of the connector 210, ends (connection pad) of the implanted conductors 211A, 211B, 211C, and 211D are electrically connected to the electrical wires 213A, 213B, 213C, and 213D via solder, respectively.

Ends (connection pad) of the implanted conductors 212A and 212B are electrically connected to the electrical wires 214A and 214B via solder, respectively.

In other cases, the outer cable 220 may be configured of three coaxial cables.

In this case, the electrical wires 213A and 213B correspond to an internal conductor and a sheath conductor of a first coaxial cable, respectively. The electrical wires 213C and 213D correspond to an internal conductor and a sheath conductor of a second coaxial cable, respectively. The electrical wires 214A and 214B correspond to an internal conductor and a sheath conductor of a third coaxial cable, respectively. A plurality of cables may be bundled into one cable.

Insulating Tube 230

The insulating tube 230 covers: the support substrate 10; the connector 210; and the outer cable 220 connected to the connector 210.

The insulating tube 230 is a resin tube with electrical insulation. As the insulating tube 230, a heat shrinkable tube is used.

As a material used to form the insulating tube 230, for example: polyimide resin; silicone resin; polyolefin resins such as polyethylene terephthalate (PET) resin, nylon resin, polyethylene resin, or polypropylene resin; or fluorine resins such as polytetrafluoroethylene (PTFE) resin are used.

Furthermore, the insulating tube 230 functions as an insertion portion of the endoscope 200. Because of this, as a material of the insulating tube 230, in addition to the aforementioned materials, rubber materials having flexibility such as urethane resins may be used.

Next, an action of the endoscope 200 described above will be described.

By applying a voltage between the light-emitting diode wirings 222A and 222B, electric power is supplied to the light-emitting diode 20 from the light-emitting diode wiring 222A through the implanted conductors 212A and 212B and the external positive terminal 13A. The light-emitting diode 20 emits light, and the light emitted from the light-emitting diode 20 is output to the outside of the imaging module 1A through the cover member 40.

An imaging object is illuminated with the light, and the reflected light from the imaging object (image) is incident to the solid-state image sensing device 30. Therefore, the solid-state image sensing device 30 captures an image of the imaging object as an image and outputs the obtained image as electrical signals. The signals output from the solid-state image sensing device 30 are received by a control device provided outside the imaging module 1A through the implanted conductors and the image-sensor wiring.

Since the aforementioned endoscope 200 according to one or more embodiments includes the imaging module 1A, it is possible to achieve miniaturization of an endoscope.

Since the endoscope 200 does not use a light guide fiber, it is possible to cause the light-emitting diode 20 to emit light at the position close to the imaging object, and the imaging object can be illuminated with the light emitted from the light-emitting diode 20. As a result, it is possible to obtain sufficient illuminance.

Endoscope 300

Figure 7:
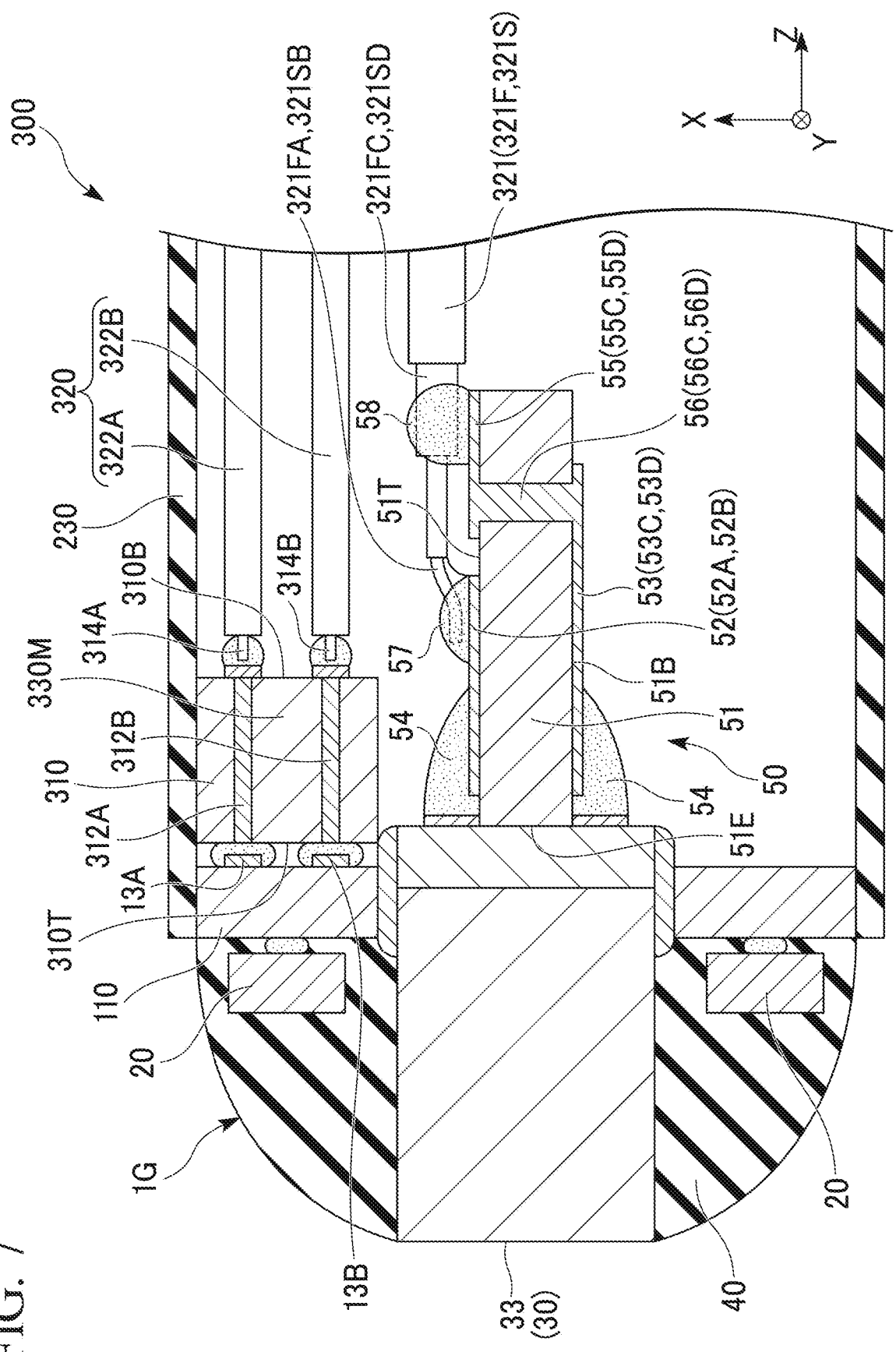
FIG. 7 is a cross-sectional view showing a relevant part of an endoscope according to one or more embodiments of the present invention.

FIG. 7 is a cross-sectional view showing a relevant part of an endoscope 300 according to one or more embodiments of the present invention.

The endoscope 300 includes: the above-mentioned imaging module 1G; a connector 310; an outer cable 320; and the insulating tube 230. Here, since the insulating tube 230 is the same as that of the above-described embodiments, the explanations thereof are omitted.

Connector 310

The connector 310 is positioned between the support substrate 110 and the outer cable 320.

The connector 310: a main body 330M formed of an insulating member; and implanted conductors 312A and 312B (fourth implanted conductor). The above-described implanted conductors are provided inside the main body 330M and extend in the Z-direction.

On an upper end face 310T of the connector 310, ends (connection pad) of the implanted conductors 312A and 312B face the imaging module 1G.

The external positive terminal 13A and the external negative terminal 13B are electrically connected to the implanted conductors 312A and 312B via solder, respectively.

Wiring Structure of Imaging Unit 50

Hereinbelow, a wiring structure of the aforementioned imaging unit 50 will be described.

The first electrical wires 52 (52A, 52B) and third electrical wires 55 (55C, 55D) located closer to the outer cable 320 than the first electrical wires 52 (52A, 52B) are formed on the base upper face 51T of the base 51 of the imaging unit 50. Through conductors 56 (56C, 56D) that penetrate through the base 51 are provided on the base 51. The through conductor 56C electrically connects the second electrical wire 53C formed on the base lower face 51B and the third electrical wire 55C. The through conductor 56D electrically connects the second electrical wire 53D formed on the base lower face 51B and the third electrical wire 55D.

In FIG. 7, the two third electrical wires 55C and 55D align in the Y-direction, and the two through conductors 56C and 56D similarly align in the Y-direction.

Outer Cable 320

The outer cable 320 includes two coaxial cables 321 (321F and 321S) and two light-emitting diode wirings 322A and 322B, that is, is configured of four cables.

Note that, the two coaxial cables 321F and 321S align in the Y-direction, and are connected to the first electrical wires 52 (52A, 52B) and the third electrical wires 55 (55C, 55D) of the aforementioned imaging unit 50.

Moreover, the light-emitting diode wirings 322A and 322B include electrical wires 314A and 314B, respectively.

Particularly, an internal conductor 321FA of the coaxial cable 321F is connected to the first electrical wire 52A via solder 57. A sheath conductor 321FC of the coaxial cable 321F is connected to the third electrical wire 55C via solder 58. An internal conductor 321SB of the coaxial cable 321S is connected to the first electrical wire 52B via the solder 57. A sheath conductor 321SD of the coaxial cable 321S is connected to the third electrical wire 55D via the solder 58.

On a lower end face 310B of the connector 210, ends (connection pad) of the implanted conductors 312A and 312B are electrically connected to the electrical wires 314A and 314B via solder, respectively.

In other cases, the light-emitting diode wirings 322A and 322B may be configured of one coaxial cable. In this case, the electrical wires 314A and 314B correspond to an internal conductor and a sheath conductor of the coaxial cable, respectively. A plurality of cables may be bundled into one cable.

Next, an action of the endoscope 300 described above will be described.

By applying a voltage between the light-emitting diode wirings 322A and 322B, electric power is supplied to the light-emitting diode 20 from the light-emitting diode wiring 322A through the implanted conductors 312A and 312B and the external positive terminal 13A. The light-emitting diode 20 emits light, and the light emitted from the light-emitting diode 20 is output to the outside of the imaging module 1G through the cover member 40.

An imaging object is illuminated with the light, and the reflected light from the imaging object (image) is incident to the solid-state image sensing device 30. Therefore, the solid-state image sensing device 30 captures an image of the imaging object as an image and outputs the obtained image as electrical signals. The signals output from the solid-state image sensing device 30 are received by a control device provided outside the imaging module 1G through the implanted conductors and the image-sensor wiring.

In the endoscope 300 according to one or more embodiments, after the base 51 and the solid-state image sensing device 30 are connected and the imaging unit 50 is thereby obtained, only by fixing the imaging unit 50 to the through hole 111, a downsized imaging module can be achieved. Accordingly, complicated mounting steps with respect to the support substrate can be omitted. As a result, it contributes to miniaturization of an endoscope.

Similar to the above-described endoscope 200, since the endoscope 300 does not use a light guide fiber, it is possible to cause the light-emitting diode 20 to emit light at the position close to the imaging object, and the imaging object can be illuminated with the light emitted from the light-emitting diode 20. As a result, it is possible to obtain sufficient illuminance.

Catheter 400

Figure 8:
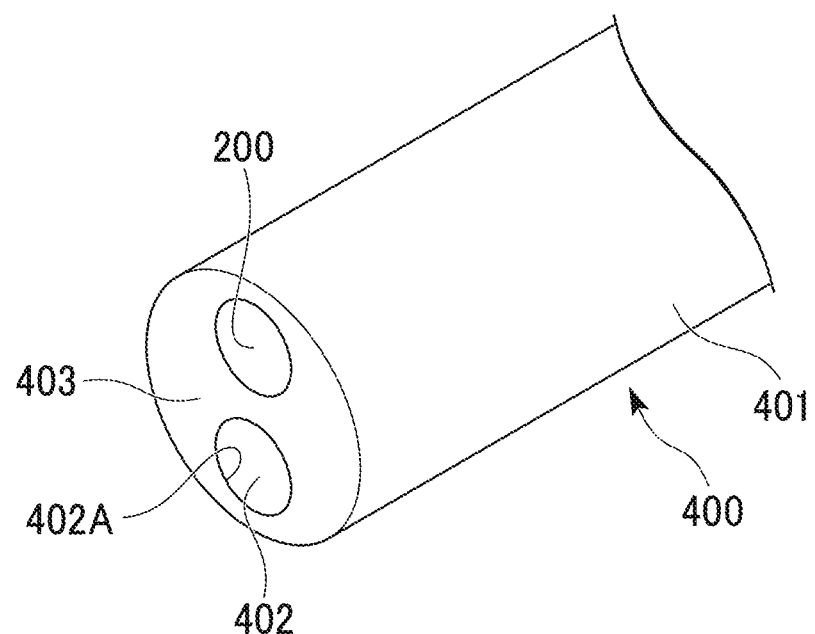
FIG. 8 is a perspective view showing a relevant part of a catheter according to one or more embodiments of the present invention.

FIG. 8 is a perspective view showing a relevant part of a catheter 400 according to one or more embodiments of the present invention.

In FIG. 8, identical symbols are used for the elements which are identical to those of the above-mentioned embodiments and the modified examples, and the explanations thereof are omitted or simplified here.

The catheter 400 shown in FIG. 8 is an imaging-module-attached catheter including the above-mentioned imaging module 1A.

The catheter 400 includes a tube 401 that is made of, for example, silicon or the like and has an insulation property. In one or more embodiments, silicon is adopted as a material used to form the tube 401, but a flexible material or a metal material other than silicon may be used.

For example, as a flexible material, silicon, polyurethane, polyethylene, polytetrafluoroethylene (PTFE, for example, Teflon (registered trademark)), or the like is adopted. As a metal material, titanium, a titanium alloy, a stainless steel, or the like is adopted. Additionally, it is not limited to a flexible material or a metal material, and ceramic material may be used as a material used to form the tube 401.

The endoscope 200 including the above-mentioned imaging module 1A according to the one or more embodiments and a channel 402 are provided inside the tube 401. That is, the tube 401 encloses the endoscope 200.

At an end face 403 of the catheter 400, an opening 402A of the channel 402 opens, and the cover member 40 and the light-incident surface 33 of the imaging module 1A are exposed. In one or more embodiments, a realizable diameter of the catheter 400 is less than or equal to, for example, approximately 5 mm (15 Fr).

The channel 402 may be used as a lumen and may be used as a working channel. In the case of using the channel 402 as a lumen, for example, a solvent medium injection lumen that ejects a solvent medium toward the front of the catheter 400 or a vacuuming lumen that removes liquid present in front of the catheter 400 can be provided in the tube 401.

Additionally, in the case of using the channel 402 as the working channel, for example, a treatment tool may be inserted into the channel 402. As the treatment tool, for example, various forcipes, a snare, a guide wire, a stent, a laser treatment tool, a high-frequency treatment tool, or the like is adopted.

Particularly, in the case where the forceps is inserted into the working channel, the catheter 400 functions as an endoscope and a catheter which is provided with a forceps channel.

According to the above-described embodiments, since the imaging module 1A having a small diameter described in the above-mentioned embodiments is provided in the catheter 400, the same effects as the effects obtained by the afore-mentioned embodiments are obtained, and it is possible to achieve the catheter 400 that has a small diameter and is provided with both the channel 402 and the imaging module.

Note that, instead of the endoscope 200, the endoscope 300 including the imaging module 1G may be applied to the catheter 400.

While embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description, and is only limited by the scope of the appended claims.

In the examples shown in FIGS. 1A and 4A, the shapes of the support substrates 10 and 110 are a circle; however, in plan view, the shape of the support substrate 10 may be a rectangle or may be a regular tetragon.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENCE NUMERALS 1A, 1B, 1C, 1D, 1E, 1F, 1G, 1H . . . imaging module, 10, 110, 120 . . . support substrate, 10B . . . second surface, 10B, 110B, 120B . . . lower face, 10T, 110T, 120T . . . upper face (first surface), 11 . . . first mounting terminal, 12 . . . second mounting terminal, 12R . . . formation region, 13A . . . external positive terminal, 13B . . . external negative terminal, 14, 14A, 14B, 14C, 14D . . . imaging external terminal, 14H, 56, 56C, 56D . . . through conductor, 18 . . . mounting region, 19 . . . fixing member, 20, 20A, 20B, 20C, 20D, 20G, 20R . . . light-emitting diode (planar light emitter), 21 . . . light-emitting face, 22 . . . light-emitter terminal, 30 . . . solid-state image sensing device, 31 . . . imaging sensor, 32 . . . glass member, 33 . . . light-incident surface, 34 . . . light-shielding portion, 35, 35A, 35B, 35C, 35D . . . image-sensing terminal, 40 . . . cover member, 41 . . . exposed area, 42, 42A, 42B . . . outer surface, 44 . . . ridge line, 50 . . . imaging unit, 51 . . . base, 51B . . . base lower face, 51E, 403 . . . end face, 51T . . . base upper face, 52, 52A, 52B . . . first electrical wire, 53, 53C, 53D . . . second electrical wire, 54, 57, 58 . . . solder, 55, 55C, 55D . . . third electrical wire, 90 . . . controller, 91 . . . first control wiring (control wiring), 92 . . . second control wiring (control wiring), 93 . . . control terminal, 111 . . . through hole, 200, 300 . . . endoscope, 210, 310 . . . connector, 210B, 310B . . . lower end face, 210T, 310T . . . upper end face, 211A, 211B, 211C, 211D, 212A, 212B, 312A, 312B . . . implanted conductor, 213A, 213B, 213C, 213D, 214A, 214B, 314A, 314B . . . electrical wire, 220, 320 . . . outer cable, 221, 221A, 221B, 221C, 221D . . . image-sensor wiring, 222A, 222B, 322A, 322B . . . light-emitting diode wiring, 230 . . . insulating tube, 230M, 330M . . . main body, 321, 321F, 321S . . . coaxial cable, 321FA, 321SB . . . internal conductor, 321FC, 321SD . . . sheath conductor, 400 . . . catheter, 401 . . . tube, 402 . . . channel, 402A . . . opening, C . . . corner, E . . . edge

The invention claimed is:

1. An endoscope comprising:
an imaging module;
a connector;

an insulating tube; and an outer cable that is connected to the connector, wherein the imaging module comprising:
- a support substrate that comprises:
    - a first surface;
    - a second surface on an opposite side of the first surface;
    - an outer-circumferential surface on an outer circumference of the support substrate; and
    - a first mounting terminal disposed on the first surface;
- a planar light emitter comprising:
    - a light-emitting face; and
    - a light-emitter terminal disposed on the first surface of the support substrate and connected to the first mounting terminal;
- a solid-state image sensing device disposed adjacent to the planar light emitter and that comprises a light-incident surface that has a quadrangular shape in plan view and that captures an image of an imaging object that is irradiated with light emitted from the light-emitting face; and
- a cover of a transparent material disposed on and in contact with the first surface of the support substrate and that covers the planar light emitter and the solid-state image sensing device, the insulating tube covers:
- the support substrate;
- the connector disposed between the support substrate and the outer cable; and
- the outer cable, and the outer-circumferential surface of the support substrate intersects the first surface and contacts an inner circumference of a tip portion of the insulating tube such that the imaging module is attached to the tip portion of the insulating tube.

2. The endoscope according to claim 1, wherein the support substrate further comprises a second mounting terminal disposed on the first surface adjacent to the first mounting terminal, and the solid-state image sensing device is disposed on the first surface of the support substrate and connected to the second mounting terminal.

3. The endoscope according to claim 2, further comprising:
- a first external terminal disposed on the second surface of the support substrate and electrically connected to the planar light emitter via the first mounting terminal; and
- a second external terminal disposed on the second surface of the support substrate and electrically connected to the solid-state image sensing device via the second mounting terminal.

4. The endoscope according to claim 1, further comprising:
- an imager that is separated from the support substrate, wherein the solid-state image sensing device is electrically connected to the imager, the support substrate comprises a through hole adjacent to the first mounting terminal and that penetrates through the support substrate, the imager is fixed in the through hole, and the solid-state image sensing device is disposed adjacent to the planar light emitter.

5. The endoscope according to claim 4, further comprising a first external terminal disposed on the second surface of the support substrate and electrically connected to the planar light emitter via the first mounting terminal.

6. The endoscope according to claim 1, wherein when seen from a cross-sectional view in a direction perpendicular to the light-incident surface, a distance from the first surface to the light-incident surface is longer than a distance from the first surface to the light-emitting face, and the cover comprises:
- an exposed area that exposes the light-incident surface, and
- an outer surface that reaches an edge of the support substrate from an outer-periphery of the light-incident surface in the cross-sectional view.

7. The endoscope according to claim 6, wherein the outer surface of the cover has a curved shape in the cross-sectional view.

8. The endoscope according to claim 1, further comprising:

planar light emitters that surround the solid-state image sensing device in plan view of the imaging module.

9. The endoscope according to claim 1, wherein the support substrate further comprises:
- a controller that controls light emission of the planar light emitter;
- a control wiring that connects the controller to the first mounting terminal; and
- a control terminal electrically connected to the controller on the second surface.

10. A catheter comprising:

the endoscope according to claim 1; and a catheter tube that:
- surrounds the imaging module,
- has an insulation property, and
- comprises a channel.

11. The endoscope according to claim 1, wherein the support substrate is circular in shape.

* * * * *